United States Patent
Klewinghaus

(10) Patent No.: US 12,311,096 B2
(45) Date of Patent: May 27, 2025

(54) SET COMPRISING EFFLUENT BAG AND ADAPTER

(71) Applicant: Fresenius Medical Care Deutschland GmbH, Bad Homburg (DE)

(72) Inventor: Juergen Klewinghaus, Oberursel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 529 days.

(21) Appl. No.: 17/786,086

(22) PCT Filed: Dec. 15, 2020

(86) PCT No.: PCT/EP2020/086192
§ 371 (c)(1),
(2) Date: Jun. 16, 2022

(87) PCT Pub. No.: WO2021/122577
PCT Pub. Date: Jun. 24, 2021

(65) Prior Publication Data
US 2023/0016493 A1  Jan. 19, 2023

(30) Foreign Application Priority Data
Dec. 19, 2019 (DE) .......... 102019135229.0

(51) Int. Cl.
*A61M 1/36* (2006.01)
*A61M 1/16* (2006.01)

(52) U.S. Cl.
CPC .......... *A61M 1/367* (2013.01); *A61M 1/1621* (2014.02)

(58) Field of Classification Search
None
See application file for complete search history.

(56) References Cited

U.S. PATENT DOCUMENTS

2008/0230450 A1* 9/2008 Burbank ............. A61M 1/1672
                                                                    210/85
2020/0230301 A1* 7/2020 Beisser ............... A61M 1/3413

FOREIGN PATENT DOCUMENTS

| DE | 102017116142 | 1/2019 |
|---|---|---|
| WO | WO 2019/016145 | 1/2019 |
| WO | WO 2021/122577 | 6/2021 |

OTHER PUBLICATIONS

International Search Report and Written Opinion in International Appln. No. PCT/EP2020/086192, dated Apr. 15, 2021, 15 pages.

* cited by examiner

*Primary Examiner* — Richard C Gurtowski
(74) *Attorney, Agent, or Firm* — Fish & Richardson P.C.

(57) ABSTRACT

The present disclosure relates to a set, encompassing or consisting of an effluent bag for receiving effluent generated during a blood treatment having precisely one closeable opening or connection to an outside of the effluent bag, wherein the effluent opening includes a first connector of a first type, or is connected to such an adapter having a line section for guiding a fluid, whereby the line section includes a second connector of the first type and a third connector of a second type, wherein the second type is different than the first type.

20 Claims, 7 Drawing Sheets

SET COMPRISING EFFLUENT BAG AND ADAPTER

CROSS-REFERENCE TO RELATED APPLICATIONS

The present application is the national stage entry of International Patent Application No. PCT/EP2020/086192, filed on Dec. 15, 2020, and claims priority to Application No. 10 2019 135 229.0, filed in the Federal Republic of Germany on Dec. 19, 2019, the disclosures of which are expressly incorporated herein in their entireties by reference thereto.

TECHNICAL FIELD

The present disclosure relates to a set having an effluent bag as described herein and methods for emptying an effluent bag.

BACKGROUND

Extracorporeal blood treatment is known from practice. Whereby the patient's blood is taken and fed along an extracorporeal blood circuit and through, for example, a blood filter. The blood filter includes a blood chamber through which blood is guided, and a dialysis liquid chamber, through which dialysis liquid is guided. Both chambers are separated from each other by a semi-permeable membrane. Blood and dialysis liquid are mostly guided through the blood filter by the counter current principle. The blood is purified in the blood filter, and on exiting the blood filter, the dialysis liquid, from now on referred to as effluent, is regarded as used and is discarded. In addition to the dialysate, the fluid to be discarded also includes filtrate (or ultra-filtrate), which includes water that has been withdrawn from the blood in the blood filter. In the following, filtrate and dialysate will be referred to individually or collectively simply as effluent.

In practice, the effluent is fed to an effluent bag via an effluent inlet line and is initially stored therein. Particularly after the treatment has ended the effluent is discarded out of the effluent bag into a sink or drain over which it is held.

SUMMARY

An aspect of the present disclosure is to specify a set having an effluent bag for use during the blood treatment.

Further, methods for emptying the effluent bag as described herein are specified.

The advantages achievable with the method described herein can also be achieved undiminished in certain embodiments with the set described herein.

The present disclosure relates to a set having an effluent bag, which is designed to receive effluent generated during a blood treatment. The effluent bag includes at least one or exactly one, optionally closeable, effluent opening to an exterior of the effluent bag. The effluent opening includes or is connected to a first connector of a first type.

Further, the set includes an adapter having a line section for guiding a fluid, e.g., effluent, whereby the line section includes a second connector of the first type and a third connector of the second type. The first and the second type are different from each other.

The present disclosure further relates to methods for emptying an effluent bag. The methods encompass providing a set as described herein, whereby the first connector (of the first type) of the effluent bag is connected to the second connector (of the first type) of the adapter in order to receive the effluent generated during a blood treatment. Additionally, the third connector (of the second type) of the adapter, is connected to a fifth connector (of the second type) of the effluent inlet line of the blood treatment apparatus. The method further encompasses detaching the first connector (of the first type) from the second connector (of the first type) and reconnecting the first connector (of the first type) and the fourth connector (of the first type) of the effluent outlet line. This is done in such a way that a fluid communication is established between the interior of the effluent bag and the interior of the effluent outlet line. This fluid communication is used to drain the effluent out of the effluent bag or to empty it.

Embodiments may include some, any, or all of the following features in any combination, unless the person skilled in the art recognizes their combination as technically impossible. Advantageous developments are also described herein.

In all of the following statements, the use of the expression "may be" or "may have" and so on, is to be understood synonymously with "preferably is" or "preferably has," and so on respectively, and is intended to illustrate embodiments.

Whenever numerical words are mentioned herein, the person skilled in the art shall recognize or understand them as indications of a numerical lower limit. Unless it leads the person skilled in the art to an evident contradiction, the person skilled in the art shall comprehend the specification for example of "one" as encompassing "at least one". This understanding is also equally encompassed as the interpretation that a numerical word, for example, "one" may alternatively mean "exactly one", wherever this is evidently technically possible for the person skilled in the art. Both are encompassed and apply herein to all used numerical words.

When it is disclosed herein that the subject-matter includes one or several features in a certain embodiment, it is also respectively disclosed herein that the subject-matter does, in other embodiments, explicitly not include this or these features, for example, in the sense of a disclaimer. Therefore, for every embodiment mentioned herein it applies that the converse embodiment, e.g., formulated as negation, is also disclosed.

Whenever an embodiment is mentioned herein, it is then an exemplary embodiment.

In some embodiments, the line section of the adapter is a non-flexible plastic line, in others it is or includes a, e.g., flexible, tubing section.

In several embodiments, the effluent opening of the effluent bag is in fluid communication with the first connector of the same, which is of the first type, via a, e.g., flexible tubing section. Hereby, in some embodiments a first inner diameter for the tubing section is provided between effluent opening and first connector of the first type.

In some embodiments, the line section of the adapter includes a second inner diameter, which is smaller than the first inner diameter.

In several embodiments the adapter, or the line section embodied as tubing section of the adapter, and/or the effluent inlet line are connected, e.g., releasably, to an exterior surface of the effluent bag. It is therefore advantageous to leave them on the effluent bag until they are needed again. Likewise the adapter can for example be detachably attached to an optionally provided holder after being used.

A holder for temporarily holding the adapter and/or the effluent inlet line may be provided not only on the effluent bag as described above, e.g., in or near a handle rail or close to the attachment openings of the effluent bag but additionally or alternatively also on the blood treatment apparatus, e.g., as an extension of its hooks or by way of an adaption of its hooks.

The previously mentioned holder may serve for holding the adapter and/or the effluent inlet line in a holding, waiting or park position until they are needed as intended.

The holder may be designed as a clip, clamp connection, feed-through mounting, and so forth.

The holder can be located in an upper part of the effluent bag (e.g., in its upper third) or on a section of the blood treatment apparatus, since the adapter and/or the effluent inlet line held by the holder therefore has less room for movement, for example for vibration, which may improve the accuracy of the values measured by the weighing apparatus.

In some embodiments the set described herein further includes an effluent outlet line for discharging effluent out of the effluent bag. Hereby, the effluent outlet line includes a fourth connector, of the first type, at the end intended for connection or at the corresponding opening. Alternatively or additionally, it includes an inner diameter which corresponds to the first inner diameter.

In some embodiments, the set further includes at least one pump or a pump head of a pump. The pump or the pump head is connected to the effluent outlet line and serves for pumping effluent out of the effluent bag. Alternatively, pumps or pump heads are provided for their connection for this purpose.

In some embodiments, the set further includes a blood treatment apparatus connected to an effluent inlet line. The effluent inlet line serves for guiding effluent generated during a blood treatment session into the effluent bag. Hereby, the effluent inlet line includes a fifth connector of the second type.

In several embodiments the blood treatment apparatus is designed as a hemodialysis apparatus, hemofiltration apparatus or as a hemodiafiltration apparatus, in particular as an apparatus for the chronic renal replacement therapy or for the continuous renal replacement therapy (CRRT).

In some embodiments, the method described herein encompasses conveying effluent out of the effluent bag, for example via the pump, after the first connector (of the first type) of the effluent bag has been connected to the fourth connector (of the first type) of the effluent outlet line.

The set described herein can optionally be understood to be a kit or drain tubing system (or a part thereof) which, in some embodiments, has further components (such as a charging station for the pump, etc.) which are not in contact with the conveyed fluid, in order to convey fluids.

In several embodiments, the effluent bag includes exactly one effluent opening, which serves as both an effluent inlet opening and as an effluent outlet opening. It may be the only liquid opening of the effluent bag, it may in fact be the only opening of the effluent bag.

In some embodiments, the effluent bag includes, for example in addition to the above-mentioned single effluent opening, a further opening, e.g., a ventilation opening, which, however, is not intended for filling the effluent bag with effluent or for emptying it. Such further openings optionally do not have connectors for connecting them to fluid lines, optionally they have connectors which, e.g., are not of the first type and/or not of the second type.

In some embodiments, the effluent bag or its effluent opening is always connected to only one tubing section, connector, or line.

In some embodiments, the effluent opening is closeable and/or provided with a cover.

In some embodiments, the effluent bag may be a container of any type, for example, a container with a flexible outer skin such as a foil, or made of foil, a container with a hard outer skin, or made of a hard outer skin such as a canister, etc.

In some embodiments, the effluent bag is connected to a drain tubing system, is arranged in a connectable manner, or is a part of a drain tubing system. The drain tubing system, or parts thereof, includes at least, or only, one line, e.g., the effluent inlet line leading to the effluent bag. The effluent inlet line may be part of the set. It is referred to herein as the inlet line because, although in use it directs effluent away from the blood treatment apparatus as the dialysate outlet line, it feeds this effluent to the effluent bag.

The effluent inlet line is used for filling the effluent bag. Clamps may be provided to prevent unwanted leakage of effluent from the blood treatment apparatus while the effluent inlet line is not connected to the effluent bag, when the effluent bag is being emptied.

Optionally, the set includes an effluent outlet line leading away from the effluent bag, but does not include a, e.g., electrically insulating, switching device via which an alternative or additional fluid connection could be established. In these embodiments the set therefore does not for example include the following; a three-way-tap (alternatively referred to as three-way-valve), a switching device made from glass or plastic, a switching device which could be switched between exactly two positions, and/or a switching device which is embodied as a multi-way tap or multi-way valve with exactly three or with more than three paths or ports.

In certain embodiments, the effluent outlet line is in conveying connection with at least one pump or a pump drive of a pump which, for example, interacts with the pump head in order to convey effluent.

In several embodiments, this pump or this pump drive includes at least one magnetically mounted or driven pump section, e.g., a pump head. This pump section or pump head is, for example, embodied as a impeller pump head or as its rotor.

In some embodiments, the pump drive, e.g., of a blood treatment apparatus or of a pump which does not belong to a blood treatment apparatus, is manually connected to the pump head of the drain tubing system.

In several embodiments, the operation of the pump drive is started and/or stopped manually.

In some embodiments, the blood treatment apparatus includes a charging station as a voltage source for the pump drive of the pump. The voltage source can be a low voltage or low current source.

In some embodiments, the set described herein encompasses the charging station for a voltage source for the pump drive of the pump, for example for a rechargeable battery.

In some embodiments, the set has at least one check valve, e.g., downstream of the optional pump, in the effluent outlet line. The non-return valve can advantageously prevent unintentional escape of effluent from the effluent outlet line, which is beneficial for cleanliness and hygiene.

In some embodiments, for example, the pump can start automatically if—manually or automatically—the effluent outlet line is or will be connected to the effluent bag. Additionally or alternatively, the pump can, for example, stop automatically if—manually or automatically—the effluent inlet line is or is will be connected to the effluent bag. The necessary sensors, devices, etc. for this purpose, may be provided.

The set may be disposable.

In several embodiments, the effluent bag is not removed or taken away from its position, the weighing apparatus, and/or the blood treatment apparatus in order for it to be emptied or for an emptying process.

In several embodiments the effluent is removed from the effluent bag without the use of a pump, and in other embodiments this is carried out through the use of a pump of the set.

In some embodiments, the method encompasses closing a shut-off element arranged in the effluent outlet line, e.g., the aforementioned clamp. This serves to shut off a fluid flow across the shut-off element.

In several embodiments, the shut-off element is only opened when the effluent pump for effluent, which is arranged in or on the effluent inlet line, has been stopped.

In some embodiments the components of the set as described herein do not include a flow divider downstream of the effluent bag.

The set may include a roller pump, for example as a pump arranged in the effluent outlet line. This roller pump may optionally be connected to precisely one inlet line and precisely one outlet line. Thereby the pump cannot separate the flow guided into it into several flows.

In some embodiments the set does not include an element downstream of the pump, which would be connected to an electrical control device, e.g., in the form of an electrically connected connector.

In several embodiments the effluent inlet line does not include a valve, in particular no check valve. The same can also apply, additionally or alternatively, for every other component or part of the set.

In some embodiments the filling and/or emptying of the effluent bag is not carried out via control or regulation of a control device or closed loop control-device.

Several or all of the embodiments may include one, several, or all of the advantages mentioned above and/or in the following.

An advantage of the set described herein, unlike in the case of conventional collecting bags, is that the effluent bag does not have to be manually removed from the machine and does not have to be emptied over a sink, which in view of the weight of the effluent bag, e.g., of up to 10 kg, represents an unpopular, time-consuming, and physically demanding activity. Rather, the effluent bag can remain on the weighing device of the blood treatment apparatus and be emptied.

The set described herein can advantageously avoid the risk that an electrically conductive contact between the liquid and the ground occurs when the contents of the effluent bag are being drained in the event of a fault, so that the permissible patient leakage currents would possibly be exceeded in the event of a fault.

In the event of a fault, with the known risks for the patient the danger of the electrical grounding of the blood treatment apparatus can be ruled out as follows: The effluent bag, the contents of which could be earthed through the drain into which the contents are pumped for emptying, is not in contact or liquid contact with the blood treatment apparatus when being emptied—due to the fact that it only has to include one opening for effluent—it may be connected to either the blood treatment apparatus or the drain, but not to both at the same time. This opening, which may be provided in a bottom area or lower area (lower third, for example) of the effluent bag, is thus used as both an inlet and an outlet.

Advantageously, the balancing device of the effluent bag, e.g., a hanging scale, cannot be influenced when using the effluent bag and a balancing cannot be falsified, especially not when using thin tube cross-sections.

A further advantage of using thin tube cross-sections may be that these cross-sections are always filled with liquid due to the surface tension of the liquids in them. So there is no problem venting the tube. An uncontrolled after-flow of liquid that could negatively influence an existing weighing system an existing or weighing device is advantageously prevented.

Since the user is forced to interrupt the treatment and must have separated the effluent inlet line from the effluent opening before it can be connected to the effluent outlet line, and this must be carried out in reverse order to be able to continue the patient's blood treatment, the set is automatically protected against misuse, which may also benefit patient safety.

In the set described herein, the flow paths between the drain or sink on the one hand and the dialyzer or patient on the other are thus advantageously electrically separated from one another, which benefits the safety of the patient.

A further advantage is the minimal effort required to implement the set described herein.

Known effluent bags that have only one opening, which are used for both filling and emptying the effluent bag, require a switching device, such as a three-way tap, through which it is possible to switch between a position for conveying in order to fill and a position for conveying in order to empty. With this type of solution further precautions must be taken in order to avoid electrical currents. In the case of the effluent bag as described herein this is not necessary. The set as described herein ensures that either only the blood treatment apparatus or only the drain can be connected to the effluent bag, without it requiring any significant material expense. Further components other than those mentioned herein are not required for the set.

Differences in diameter which exist between known disposable components in the area of the effluent bag are overcome using suitable connectors and/or adapted diameters.

The adapter of the set also allows known effluent bags with only one effluent opening to be used on blood treatment apparatuses which were not intended to be used together with such effluent bags, which is why this has not been possible until now.

Through its adapter, the set described herein offers a technical solution that can be fitted to existing solutions without changing the latter. Advantageously, a new approval, e.g., of the effluent inlet line, is not necessary, if it should be used for example in a different design or length than before, or also of the blood treatment apparatus connected to it as a medical apparatus, which saves effort, costs and expenditure.

BRIEF DESCRIPTION OF THE FIGURES

The present invention is exemplarily explained with regard to the accompanying drawings, in which same reference numerals refer to the same or similar components. In the figures the following applies.

DETAILED DESCRIPTION

Figure 1:
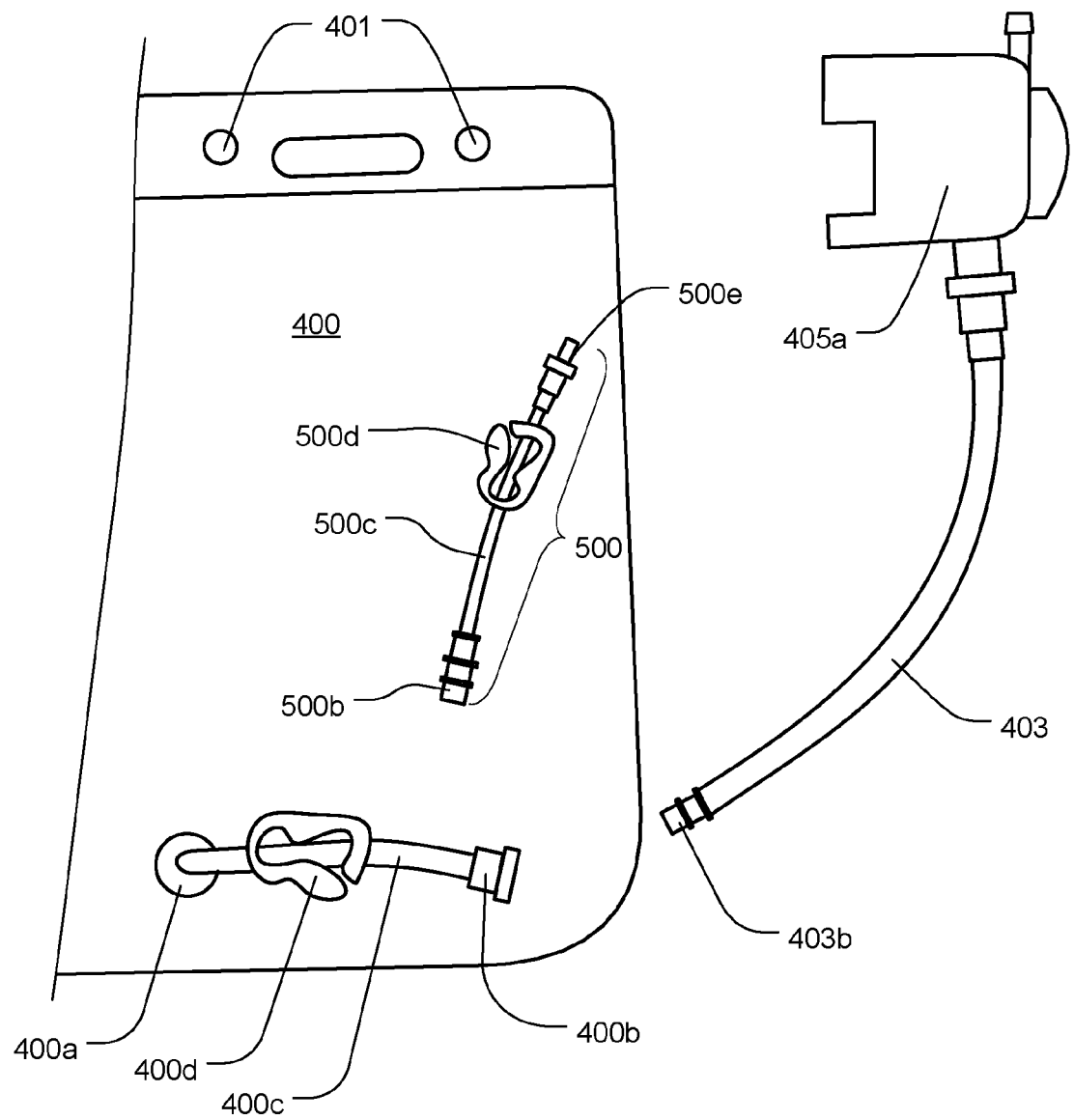
FIG. 1 shows a set in a first embodiment.

FIG. 1 shows a set including or consisting of an effluent bag 400 and an adapter 500.

The effluent bag 400 serves during use for receiving the effluent generated during a blood treatment. It includes a closeable effluent opening 400a connecting the interior of the effluent bag 400 to the exterior thereof.

In order to connect the effluent opening 400a the latter includes or is connected to a first connector 400b of a first type.

The clamp 400d shown here, purely provided optionally, may serve for closing the effluent opening 400a. It is provided here on a tubing section 400c, also purely optionally provided, which connects the effluent opening 400a to the first connector 400b of the first type. If no such tubing section 400c is provided, then the first connector 400b, of the first type, could be directly connected to the effluent opening 400a.

The adapter 500 includes a line section, here embodied as a tubing section 500c having two openings through which fluid is conveyed into or out of the adapter 500 when it is in use, and which are connected to each other via the tubing section 500c. The lumen of the tubing section 500c can be closed using an optional clamp of the adapter 500.

Each of the aforementioned two openings includes a connector, specifically a second connector 500b, of the first type, and a third connector 500e of the second type.

The second connector 500b is, as mentioned, like the first connector 400b of the first type. This can be a female and a male counterpart, which is why the first connector 400b, of the first type, and the second connector 500b, of the first type, are not identically embodied. However, they can still be connected to each other, so here they are considered connectors of the same type. However, a connector of the first type would not be connectable to a connector of a second type.

The third connector 500e is such a connector of the second type.

To the right of FIG. 1 is an effluent outlet line 403. When in use, the effluent outlet line 403 is connected to a pump head 405a of a pump 405 shown in FIG. 6 and FIG. 7. The pump serves for pumping effluent out of the effluent bag 400.

The effluent outlet line 403 includes a fourth connector 403b of the first type.

Figure 4:
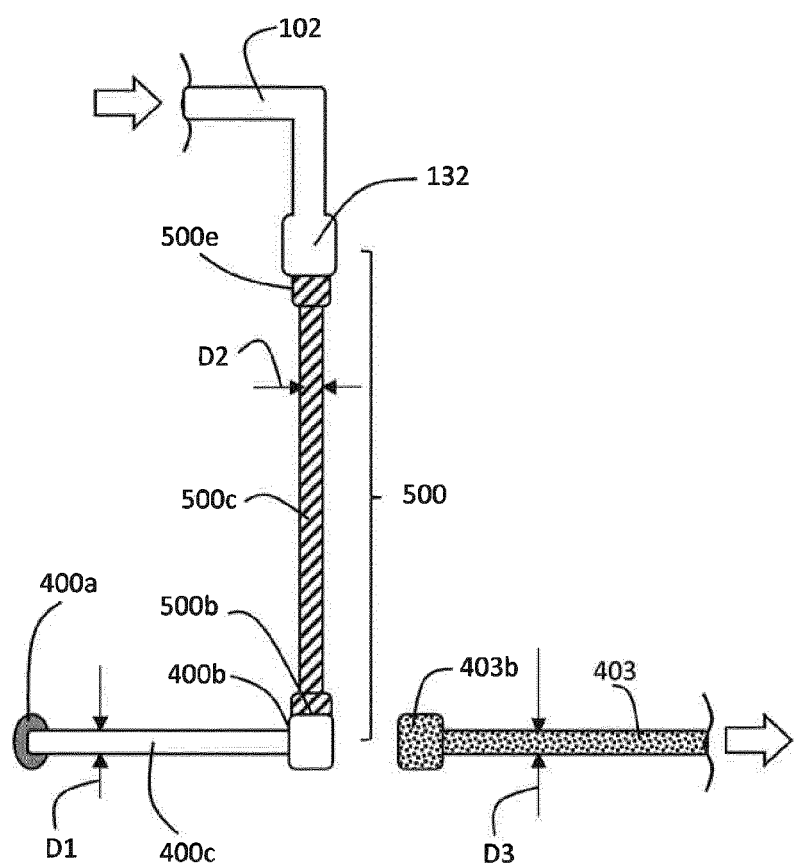
FIG. 4 shows in a highly simplified representation a part of a set having line sections, tubing sections and connectors.

Therefore, from the connectors shown in FIG. 1 the following pairings can be connected as intended in a fluid-tight manner: first connector 400b to second connector 500b, both of the first type; first connector 400b to the fourth connector 403b, both of the first type (as described in more detail in FIG. 4).

The effluent bag 400 may include attachment (or mounting) openings 401, via which it may be hung for example, on hooks of a weighing apparatus of the blood treatment apparatus 100.

Figure 2:
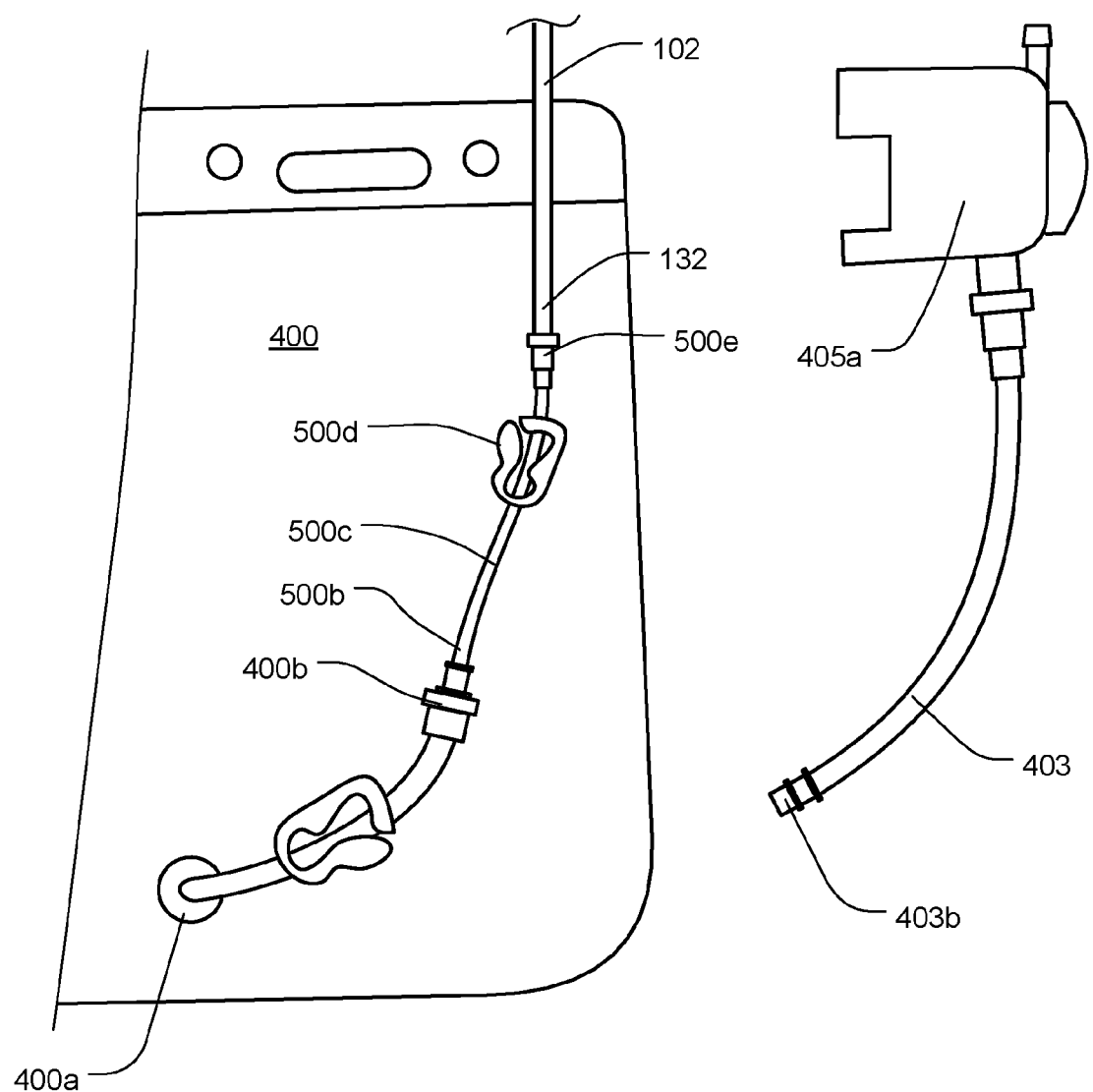
FIG. 2 shows the set of FIG. 1, whereby the adapter is connected to the first connector, of the first type, of FIG. 1, via its second connector of the first type.

FIG. 2 shows the set of FIG. 1, wherein the adapter 500 is connected to the first connector 400b of the first type via its second connector 500b of the first type.

The third connector 500e of the second type is connected as intended to the fifth connector 132 of the second type, provided on the effluent inlet line 102 for filling the effluent bag 400, as indicated in FIG. 2.

The connection status shown in FIG. 2 serve for filling the effluent bag 400.

Figure 3:
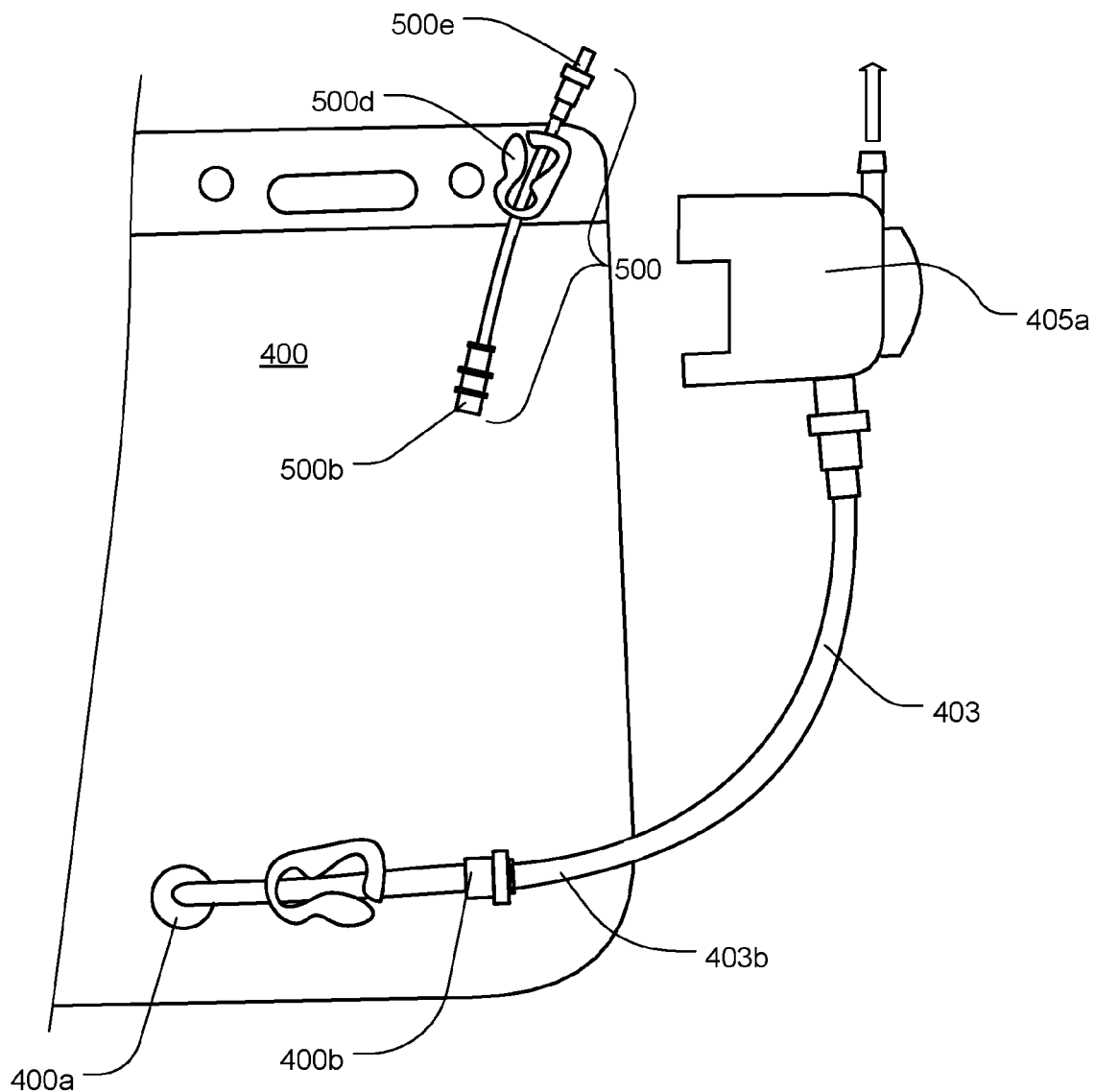
FIG. 3 again shows the set of FIG. 1, whereby the adapter of the set is no longer connected in fluid communication with the effluent bag of FIG. 2.

FIG. 3 further shows the set of FIG. 1, whereby the adapter 500 is no longer in fluid communication with the effluent bag 400.

Rather, FIG. 3 shows a connection status, in which the effluent bag 400 could be emptied via the effluent outlet line 403, which in turn could be connected, directly or indirectly, to the drain 600. For this purpose, the first connector 400b of the first type and the fourth connector 403b of the first type are connected to each other.

In the overview of FIGS. 2 and 3, it can be seen that there is only one connection possibility at a time, e.g., either that of FIG. 2 or that of FIG. 3. Thereby, when the effluent bag 400 is emptied, it is completely fluidically separated from the blood treatment apparatus 100 or its effluent inlet line 102 or its connector, hereinafter referred to as the fifth connector 132 of the second type.

FIG. 4 shows in a highly simplified representation a part of a set having line sections 102, 403, tubing sections 400c, 500c, and connectors 132, 500e, 400b, 500b, 403b. Thereby, the connectors 400b, 500b, 403b are of the first type, the connectors 132 and 500e are of the second type.

The adapter 500 of the set is indicated using hatched shading. During the blood treatment using the blood treatment apparatus 100 generated effluent is conveyed into the adapter 500 via the effluent inlet line 102 and the fifth connector 132 of the second type. This is illustrated by the arrow on the left. The effluent outlet line 403 having the fourth connector 403b, of the first type is shown using dotted shading. When this is connected to the effluent bag 400 the effluent is conveyed into a drain 600. This is illustrated using the arrow on the right.

Figure 7:
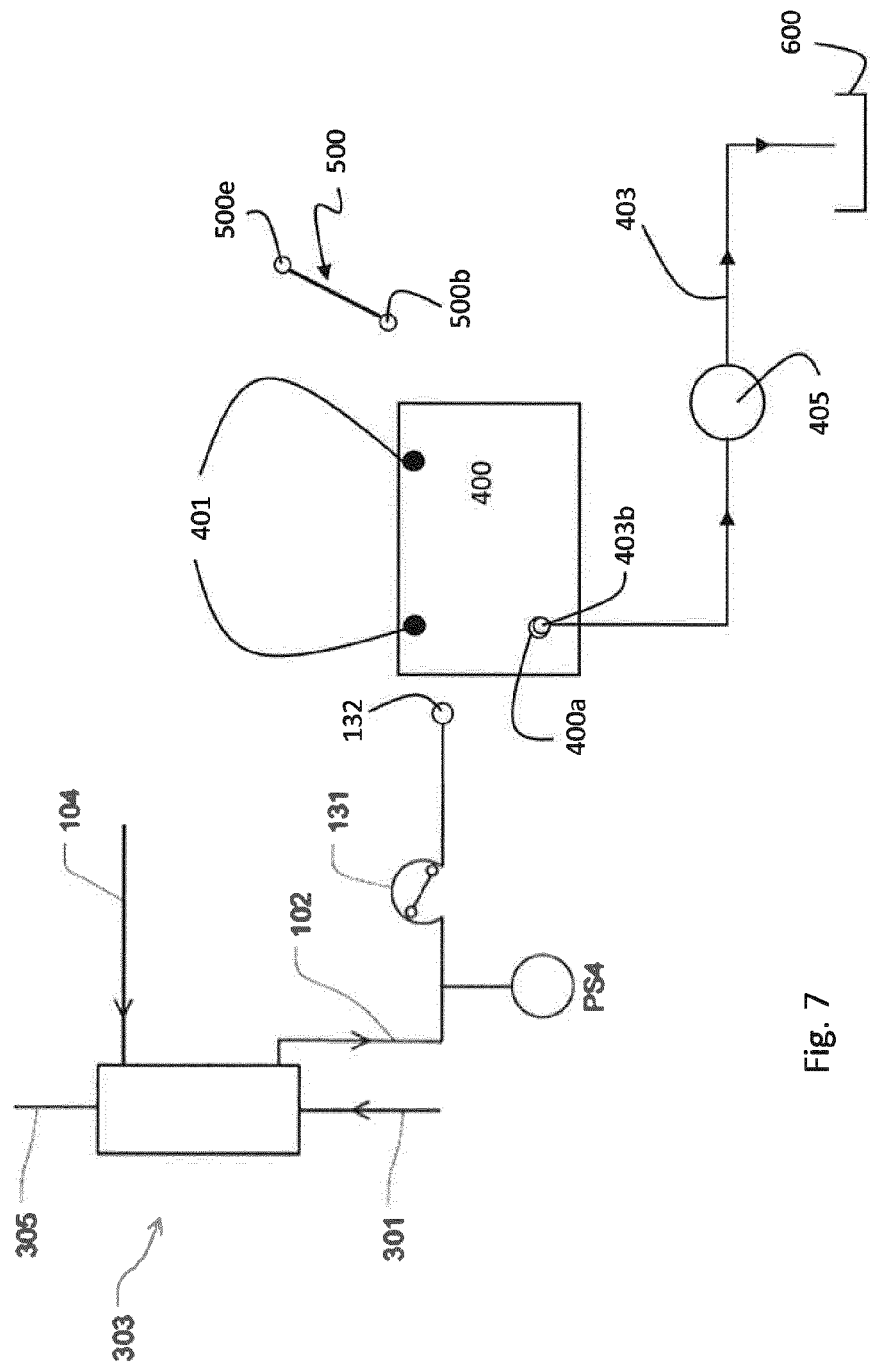
FIG. 7 shows the set of FIG. 6, while effluent is being discharged from the effluent bag.

Of the connectors shown in FIG. 4 the following pairings can be connected to each other in a particularly fluid-tight manner as intended:

first connector 400b to second connector 500b, both of the first type (as illustrated);

third connector 500e to the fifth connector 132, both of the second type (as illustrated), furthermore first connector 400b to the fourth connector 403b, both of the first type (not illustrated here, see FIG. 3 and FIG. 7).

The aforementioned connectors can, for example, be connected to each other, because they include, for example, the same shape or complementary shapes and/or sizes.

The aforementioned connectors can, for example, be connected to each other, as being of the same type they are intended to be connected to each other (but optionally still designed as male and female counterparts).

The aforementioned connectors can be connected to each other without using tools, additional material, etc.

Connectors which are not meant to be connectable to each other, e.g., in a fluid-tight manner, are not accidentally connected to each other.

The third connector 500e of the second type cannot be connected in a fluid-tight manner to any of the connectors 400b, 500b, and 403b, of the first type.

The inner diameter of the tubing section 400c, herein referred to as first inner diameter D1, is bigger than the second diameter D2 of the tubing section 500c, herein referred to as D2.

The inner diameter D2 of the tubing section 500c is smaller than the inner diameter D3 of the effluent outlet line 403.

In some embodiment, the inner diameter D1 of the tubing section 400c and the inner diameter D3 of the effluent outlet line 403 may be the same.

In some embodiments, the inner diameter of the effluent inlet line 102 and the inner diameter D2 of the adapter 500 may be the same.

Purely as an example, the third connector 500e of the second type is male, e.g., a male Luer-lock connector. Also the second connector 500b of the first type is, purely as an example, male, e.g., a male Luer-lock connector. The same optionally applies to the fourth connector 403b of the first type. It can—like other connectors herein—be a Luer-lock connector or be of a different design, e.g., a COLDER-connection, i.e., an embodiment of a quick coupling, designed as a plug connector with a radial seal and spring-loaded lock.

In contrast, the first connector 400b of the first type can be female, e.g., a female Luer-lock connector.

In several embodiments, the first or third inner diameters D1 or D3 can respectively be between 5 mm and 15 mm, preferably 10 mm.

The second inner diameters can be between 3 mm and 7 mm, preferably 4.3 mm.

Figure 5:
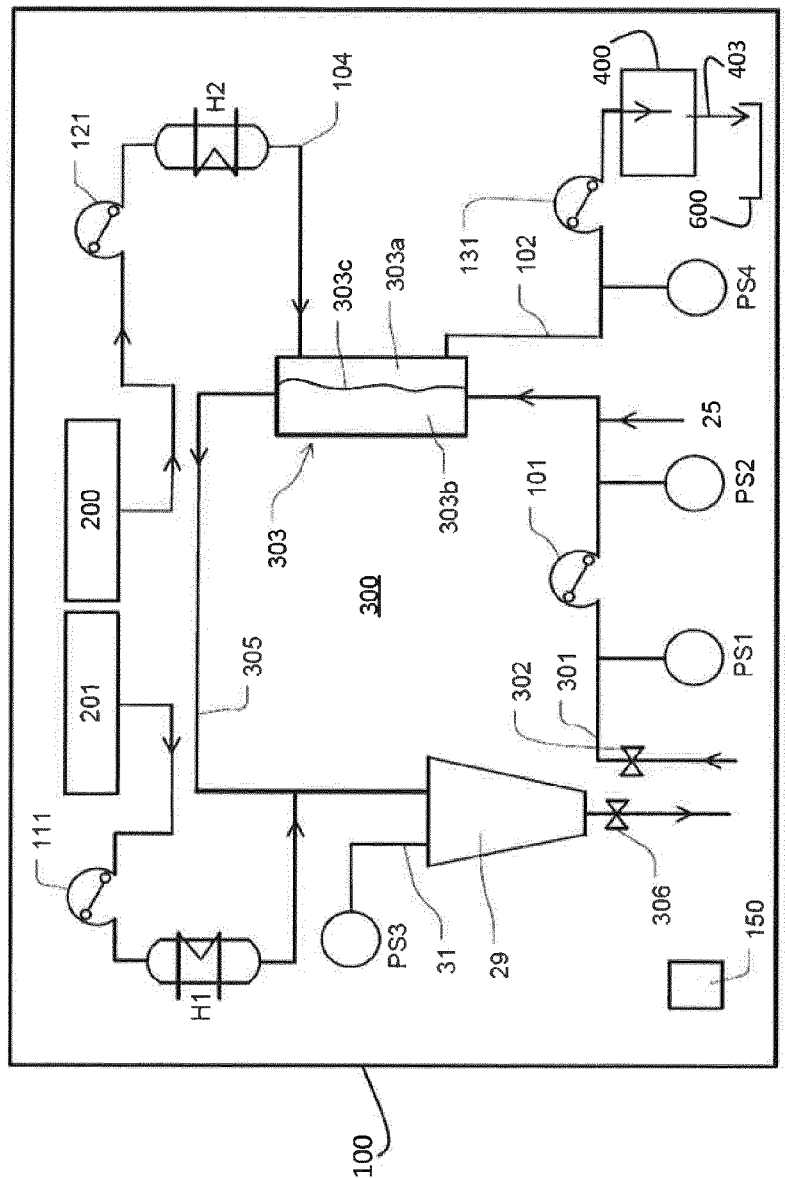
FIG. 5 shows in a highly simplified representation, a blood treatment apparatus of a set as described herein, connected to an extracorporeal blood circuit and to an effluent bag of the set.

FIG. 5 shows in a highly simplified representation a blood treatment apparatus 100 of a set described herein, connected to an extracorporeal blood circuit 300 and an effluent bag 400 of the set.

The extracorporeal blood circuit 300 includes a first line 301, here in the form of an arterial line section.

The first line 301 is in fluid communication with a blood treatment device, here for example a blood filter or a dialyzer 303. The blood filter 303 includes a dialysis liquid chamber 303a and a blood chamber 303b, which are separated from each other by a mostly semi-permeable membrane 303c.

The extracorporeal blood circuit 300 further includes at least one second line 305, here in the form of a venous line section. Both the first line 301 and the second line 305 may be used to connect them to the vascular system of the patient, not shown.

The first line 301 is optionally connected to a (first) tubing clamp 302 for blocking or closing the line 301. The second line 305 is optionally connected to a (second) tubing clamp 306 for blocking or closing the line 305.

The blood treatment apparatus 100 represented in FIG. 1 only schematically and only by some of its devices includes a blood pump 101. During the patient's treatment, the blood pump 101 conveys blood through sections of the extracorporeal blood circuit 300 and towards the blood filter or dialyzer 303, as indicated by the small arrows that generally indicate the direction of flow in each of the figures.

Fresh dialysis liquid is pumped from a source 200 along the dialysis liquid inlet line 104 into the dialysis liquid chamber 303a, by a pump for dialysis liquid 121, which may be designed as a roller pump or as an otherwise occluding pump. The dialysis liquid leaves the dialysis liquid chamber 303a as dialysate, possibly enriched by filtrate, towards the drain 600 and is herein referred to as effluent.

The source 200 may be, for example a bag or a container. The source 200 may further be a fluid line out of which from the online and/or continuously generated or mixed liquid is provided, for example a hydraulic output or hydraulic connection of the blood treatment apparatus 100.

A further source 201 with substitute may be optionally provided. It may correspond to the source 200 or be a separate source.

An only roughly indicated control device or closed loop control-device 150 can be configured to carry out the aforementioned method. Optionally it may be carried out manually.

At the bottom right of FIG. 5, is indicated where the effluent outlet line 403 with the effluent bag 400 shown in FIG. 1 is optionally connected to the blood treatment apparatus 100.

In addition to the aforementioned blood pump 101, the arrangement shown in FIG. 5 further includes purely optionally a series of other pumps, in each case optional, namely the pump 111 for substitute, the pump 121 for dialysis liquid, and the pump 131 for the effluent.

The pump 121 is provided to guide dialysis liquid, out of a source 200, for example a bag, via an optional existing bag heater H2, having a bag to the blood filter 303, via a dialysate liquid inlet line 104.

The thus supplied dialysis liquid exits from the blood filter 303 via a dialysate outlet line 102, supported by the pump 131, and may be discarded.

Upstream of blood pump 101k an optional arterial sensor PS1 is provided. It measures the pressure in the arterial line, during the patient's treatment.

Downstream of the blood pump 101, but upstream of the blood filter 303 and, if provided, upstream of a coupling site 25 for Heparin, a further optional pressure sensor PS2 is provided. It measures the pressure upstream of the blood filter 303 ("pre-hemofilter").

Again, a further pressure sensor may be provided as PS4 downstream of the blood filter 303, e.g., upstream of the pump 131 in the dialysate outlet line 102 in order to measure the filtrate pressure of the blood filter 303.

Blood, which leaves the blood filter 303, passes through an optional venous blood chamber 29, which includes a ventilation or venting or de-aeration device 31 and can be in fluid communication with a further pressure sensor PS3.

The exemplary arrangement, shown in FIG. 1 includes a control device or closed-loop control device 150. It can be in cable or wireless signal communication with any of the components referred to herein—e.g., at least to the blood pump 101—in order to control or regulate the blood treatment apparatus 100. It is optionally configured to carry out the herein referred to method.

The optional pump 111 is provided to guide substitute out of the optional source 201, for example a bag, via an optional available bag heater H1 having a heat bag, to the second line 305.

Figure 6:
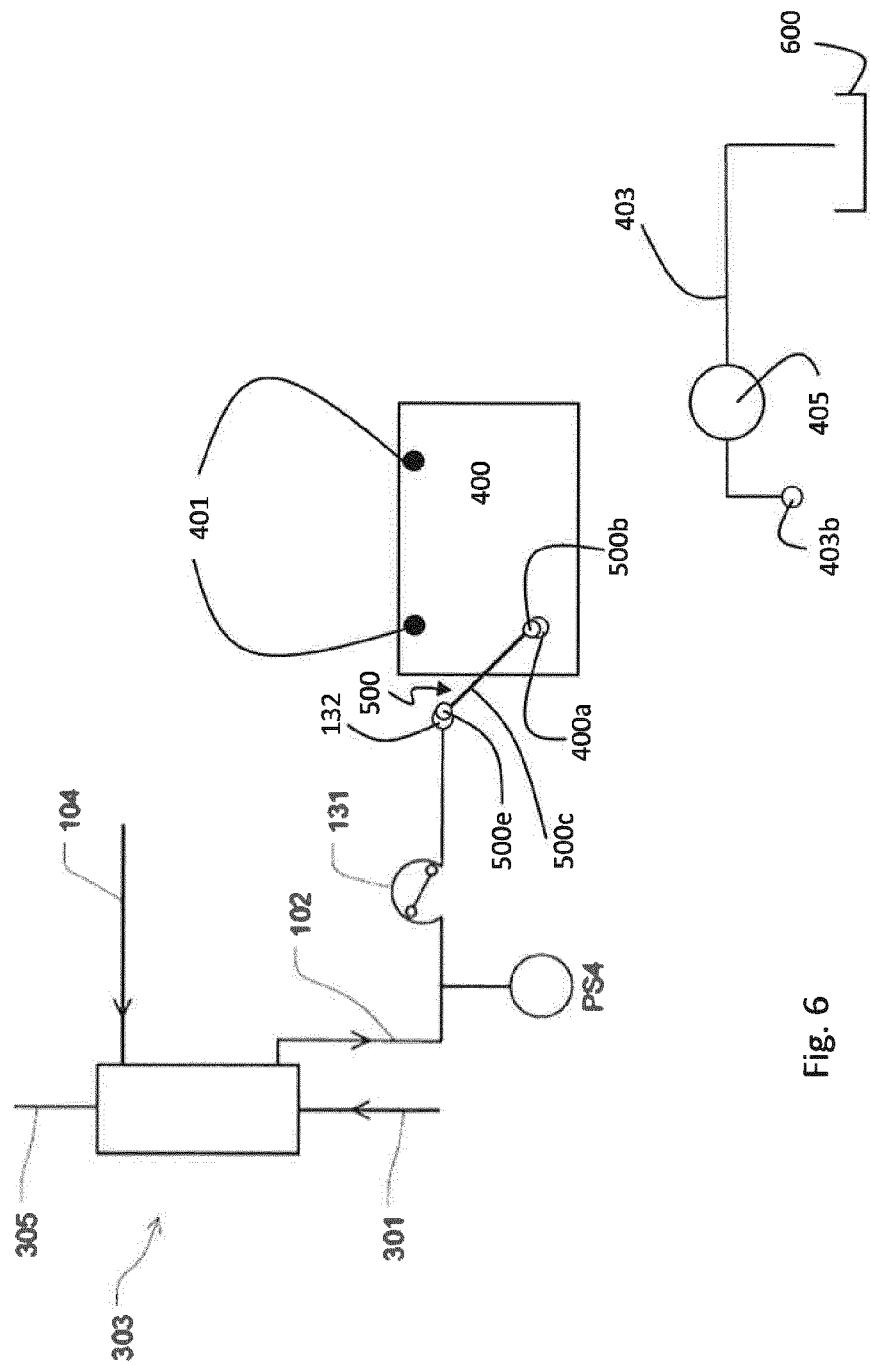
FIG. 6 shows in a simplified representation, a set having an effluent bag, while effluent is being guided to the effluent bag.

FIG. 6 shows in a highly simplified representation a set with its effluent bag 400 at a moment in which the effluent bag 400 is supplied with effluent.

The effluent outlet line 403 may include an optional pump 405 or be connected to one and finally feed into the drain 600.

The pump 405 is arranged downstream of the effluent bag 400, but upstream of the drain 600.

The pump 405, which as first shown in FIG. 4, optionally includes or consists of at least a pump drive and a pump head 405a, is shown in FIG. 6, in the not in operation position ("OFF"), as the effluent outlet line 403 is not guiding any effluent which could be discharged into the drain 600 by means of the pump 405.

The pump 405 can in any embodiment be a roller pump. Alternatively, in any embodiment it is not a roller pump, but for example, an impeller pump or a membrane pump.

The effluent outlet line 403 is fluidically connected with the pump head 405a of the pump 405. The pump head 405a may be part of the effluent outlet line 403, that again may be a disposable tube. The pump head 405a can be mounted positioned, which can simplify its connection to other sections of the pump 405 and to advantageously help to prevent the transmission of current between the connected components.

The pressure side of the pump head 405a is connected to a line which can be understood to be a continuation of the effluent outlet line 403 or as a further tubing section.

The pump drive of the pump 405, which interacts with the pump head 405a in order to form the pump 405, can be part of the blood treatment apparatus 100. However it may optionally be part of a, for example mobile, device. The latter can have no electrical and/or physical contact with the blood treatment apparatus. For example, the device can be powered by a, e.g., rechargeable voltage source, which is not connected to the power supply of the blood treatment device and/or the hospital when the pump is in operation.

The effluent bag 400 can be connected to a weighing device for weighing its weight or the weight of the fluid it receives or for determining a change in weight. For example, the effluent bag 400 may be placed a collection bag on a weighing surface of the weighing device or may be hung by its attachment openings 401 on one or more weighing hooks of the blood treatment device 100, not shown.

As can be seen from FIG. 6, the set optionally includes a pump 405. In alternative embodiments the effluent is emptied from the effluent bag 400 without support from the pump, e.g., by gravity alone.

A non-return valve, not shown, may be provided in the effluent inlet line 102.

The set, e.g., and its adapter 500, is used in the position shown in FIG. 6, namely for filling the effluent bag 400.

The second connector 500b of the first type of the adapter 500 is connected to the connector 400b of the first type of the effluent bag 400.

The third connector 500e of the second type of adapter 500 is connected to the fifth connector 132 of the second type of the effluent inlet line 102.

The level of effluent inside the effluent bag 400 increases at this stage.

Liquid flows are indicated by arrows.

FIG. 7 shows the set of FIG. 6 while effluent is being discharged from the effluent bag 400.

In order to empty effluent bag 400, the pump 131 for the effluent has been stopped. As a result, the liquid-filled section of the effluent inlet line 102 running upstream of the pump 131 is electrically isolated from the section of the liquid-filled effluent inlet line 102 running downstream of the pump 131. Thus, the permitted thresholds for patient leakage currents are not reached. Thereby, the stationary, not running, occluding pump 131 (roller pump) isolates the liquid columns upstream of pump 131 and downstream of pump 131 from each other. The prevailing gravity may also contribute to this by causing the liquid column present downstream of the pump 131 to break off or move towards the effluent bag 400.

In order to empty the effluent bag 400 the effluent inlet line 102 is separated from the effluent bag 400. This can be done via the fifth connector 132 of the second type, which in FIG. 6, still connects the section of the liquid-filled effluent inlet line 102 running downstream of the pump 131 to the effluent bag 400. The effluent inlet line 102 can also be disconnected using a clamp (not shown in FIG. 6).

After its separation, the effluent inlet line 102 can optionally be closed with a cap and/or closed downstream of the pump 131 using a manual hose clamp (cap and hose clamp are not shown in FIG. 7).

For example, when the pump 405 is an impeller pump, which is not self-priming, it may be of advantage if the effluent outlet line 403 is arranged inclining upwards towards the drain 600. Alternatively or optionally, the effluent outlet line 403 runs in a sloping downwards between a shut-off element (not indicated) and the pump 405, so that air bubbles can rise up and may be directed towards the drain 600 or alternatively towards the effluent bag 400.

Using this method, explained with reference to FIG. 7, the effluent bag 400 can advantageously only be emptied after the effluent inlet line 102 has been separated from the effluent bag 400, with the aim of being electrically safe, (i.e., to safely ensure that patient leakage currents fall below the threshold values even in the event of a fault).

The pump 405 may be embodied as a pump as disclosed in the German patent application which was filed for the applicant of the present application at the German Patent and Trademark Office under the file number DE 102017122804.7 with the filing date Sep. 29, 2017, the disclosure of which is hereby incorporated in its entirety. However, alternatively, another pump may be used.

Optionally, the set does not include a flow divider downstream of the effluent bag 400. The set can, however, include a roller pump, for instance as pump 405. The roller pump can optionally be connected to exactly one inlet line and to exactly one outlet line. This means that the pump obviously cannot divide the flow leading into it into several flows.

Optionally, the set does not include a connector downstream of the pump 405.

Optionally, the set which continues downstream of the effluent bag 400 and/or upstream of the pump 405 does not include an element which would be connected to an electrical control device, for example, in the form of an electrically connected connector.

LIST OF REFERENCE NUMERALS 25 addition point for Heparin (optional)
29 venous blood chamber (optional)
31 ventilation device
100 blood treatment apparatus
101 blood pump
102 dialysate outlet line, effluent inlet line
104 dialysis liquid inlet line
111 pump for substituate
121 pump for dialysis liquid
131 pump for dialysate or effluent
132 in effluent inlet line
132 fifth connector of the second type
150 control device or closed-loop control device
200 dialysis liquid source
201 substituate source, optional
300 extracorporeal blood circuit
301 first line (arterial line section)
302 (first) tubing clamp
303 blood filter or dialyzer 303a dialysis liquid chamber
303b blood chamber
303c semi-permeable membrane
305 second line (venous line section)
306 (second) tubing clamp
400 effluent bag
400a effluent inlet or effluent outlet opening; effluent opening
400b first connector of the first type
400c tubing section
400d clamp
401 attachment or mounting openings
403 effluent outlet line
403b fourth connector of the first type
405 pump in effluent outlet line
405a pump head
500 adapter
500b second connector of the first type
500c tubing section
500d clamp
500e third connector of the second type
600 drain or sink
D1, D2, D3 inner diameter
H2 bag heater having a bag (dialysis liquid)
H1 bag heater having a bag (substitute)
PS1, PS2 arterial pressure sensor (optional)
PS3 pressure sensor (optional)
PS4 pressure sensor for measuring filtrate pressure

The invention claimed is:

1. A set comprising:
an effluent bag for receiving effluent generated during a blood treatment, having exactly one closeable effluent opening to an exterior of the effluent bag, wherein the effluent opening has or is connected to a first connector of a first type; and
an adapter having a line section for guiding a fluid, wherein the line section comprises a second connector of the first type, and a third connector of a second type, which is different than the first type.

2. The set according to claim 1, wherein the line section of the adapter is or comprises either a non-flexible plastic line or a tubing section.

3. The set according to claim 1, wherein the effluent opening is in fluid communication with the first connector of the first type, via a tubing section that comprises a first inner diameter between the effluent opening and the first connector of the first type.

4. The set according to claim 3, wherein the line section of the adapter comprises a second inner diameter which is smaller than the first inner diameter.

5. The set according to claim 1, wherein the adapter is connected to an outer surface of the effluent bag.

6. The set according to claim 5, wherein the line section of the adapter comprises a tubing section that is connected to the outer surface of the effluent bag.

7. The set according to claim 6, wherein the line section of the adapter is detachably connected to the outer surface of the effluent bag.

8. The set according to claim 1, further comprising an effluent outlet line for discharging effluent out of the effluent bag, wherein the effluent outlet line comprises a fourth connector, of the first type, and/or an inner diameter which substantially or exactly corresponds to the first inner diameter.

9. The set according to claim 8, further comprising at least one pump or a pump head of a pump, connected to the effluent outlet line for pumping effluent out of the effluent bag, or provided for connection to the effluent outlet line.

10. The set according to claim 1, further comprising a blood treatment apparatus having an effluent inlet line for guiding effluent generated during a blood treatment session into the effluent bag, wherein the effluent inlet line comprises a fifth connector of the second type.

11. The set according to claim 10, wherein the blood treatment apparatus is a hemodialysis apparatus, hemofiltration apparatus or hemodiafiltration apparatus.

12. The set according to claim 10, wherein the blood treatment apparatus is an apparatus for chronic renal replacement therapy or for continuous renal replacement therapy (CRRT).

13. A method for emptying an effluent bag, wherein the method comprises:
providing a set comprising:
an effluent bag for receiving effluent generated during a blood treatment, having exactly one closeable effluent opening to an exterior of the effluent bag, wherein the effluent opening has or is connected to a first connector of a first type;
an adapter having a line section for guiding a fluid, wherein the line section comprises a second connector of the first type, and a third connector of a second type, which is different to the first type;
an effluent outlet line for discharging effluent out of the effluent bag, wherein the effluent outlet line comprises a fourth connector, of the first type; and
a blood treatment apparatus having an effluent inlet line for guiding effluent generated during a blood treatment session into the effluent bag, wherein the effluent inlet line comprises a fifth connector of the second type;
wherein the first connector of the effluent bag for receiving the effluent generated during a blood treatment in the effluent bag is connected to the second connector of the adapter, and wherein the third connector of the adapter is connected to the fifth connector of the effluent inlet line of the blood treatment apparatus;
separating the first connector from the second connector; and
connecting the first connector to the fourth connector of the effluent outlet line to discharge the effluent out of the effluent bag in such a way that a fluid communication is established between the inside of the effluent bag and the inside of the effluent outlet line.

14. The method according to claim 13, further comprising conveying effluent out of the effluent bag, after the first connector of the effluent bag has been connected to the fourth connector of the effluent outlet line.

15. The method according to claim 13, wherein the line section of the adapter is or comprises either a non-flexible plastic line or a tubing section.

16. The method according to claim 15, wherein the effluent opening is in fluid communication with the first connector of the first type, via a tubing section that comprises a first inner diameter between the effluent opening and the first connector of the first type.

17. The method according to claim 16, wherein the line section of the adapter comprises a second inner diameter that is smaller than the first inner diameter.

18. The method according to claim 13, wherein the adapter is connected to an outer surface of the effluent bag.

19. The method according to claim 18, wherein the line section of the adapter comprises a tubing section that is connected to the outer surface of the effluent bag.

20. The method according to claim 18, wherein the line section of the adapter is detachably connected to the outer surface of the effluent bag.

* * * * *